United States Patent
Nespor

(10) Patent No.: US 11,311,330 B2
(45) Date of Patent: Apr. 26, 2022

(54) PORTABLE DEVICE USED ESPECIALLY FOR ELECTROFULGURATION AND ELECTRODESICCATION

(71) Applicant: COMPEX SPOL. S. R. O., Brno (CZ)

(72) Inventor: Radek Nespor, Brno (CZ)

( * ) Notice: Subject to any disclaimer, the term of this patent is extended or adjusted under 35 U.S.C. 154(b) by 234 days.

(21) Appl. No.: 15/575,347

(22) PCT Filed: May 18, 2016

(86) PCT No.: PCT/CZ2016/050014
§ 371 (c)(1),
(2) Date: Nov. 18, 2017

(87) PCT Pub. No.: WO2016/184442
PCT Pub. Date: Nov. 24, 2016

(65) Prior Publication Data
US 2018/0147001 A1    May 31, 2018

(30) Foreign Application Priority Data
May 19, 2015    (CZ) .................................. CZ2015-333

(51) Int. Cl.
*A61B 18/00*    (2006.01)
*A61B 18/14*    (2006.01)
(Continued)

(52) U.S. Cl.
CPC ...... *A61B 18/1402* (2013.01); *A61B 18/1206* (2013.01); *A61B 2017/00199* (2013.01);
(Continued)

(58) Field of Classification Search
CPC .................. A61B 18/18; A61B 18/042; A61B 2018/1213; A61B 2018/1226;
(Continued)

(56) References Cited

U.S. PATENT DOCUMENTS 4,878,493 A    11/1989   Pasternak et al.
5,873,855 A    2/1999    Eggers et al.
(Continued)

FOREIGN PATENT DOCUMENTS

WO    2009050753 A1    4/2009
WO    2014060854 A1    4/2014

OTHER PUBLICATIONS

Cordero, Ismael. "Electrosurgical units—how they work and how to use them safely." Community eye health vol. 28,89 (2015): 15-6. (Year: 2015).*

(Continued)

*Primary Examiner* — Jaymi E Della
*Assistant Examiner* — Rachel A. Vierra
(74) *Attorney, Agent, or Firm* — Krishna Kalidindi

(57) ABSTRACT

A portable electrocauter used especially for electrofulguration, electrodesiccation and electrocoagulation contains a source of energy and an applicator. The electrocauter is provided with the source of DC with the maximal current of 1 mA and voltage between 0.8 to 12 kV. The applicator is provided with precisely aiming finish and the patient is conductively connected with the equipment by disposable (Continued)

grounding electrode while the output of the discharge between the working electrode and the surface of the skin is in the range of 0.3 to 4.0 W.

3 Claims, 3 Drawing Sheets

(51) Int. Cl.
  *A61B 18/12* (2006.01)
  *A61B 17/00* (2006.01)
  *A61B 18/16* (2006.01)

(52) U.S. Cl.
  CPC ............... *A61B 2018/0047* (2013.01); *A61B 2018/00452* (2013.01); *A61B 2018/00589* (2013.01); *A61B 2018/00595* (2013.01); *A61B 2018/1213* (2013.01); *A61B 2018/1226* (2013.01); *A61B 2018/1266* (2013.01); *A61B 2018/162* (2013.01)

(58) Field of Classification Search
  CPC .. A61B 2018/1266; A61B 2018/00452; H05H 1/24; H05H 1/2406; H05H 1/48; H05H 2245/122
  See application file for complete search history.

(56) References Cited

U.S. PATENT DOCUMENTS

| | | | | |
|---|---|---|---|---|
| 6,890,332 | B2* | 5/2005 | Truckai | A61B 17/22004 128/898 |
| 7,127,288 | B2* | 10/2006 | Sturman | A61N 1/08 607/2 |
| 8,321,009 | B2* | 11/2012 | Rosemberg | A61N 1/044 604/20 |
| 2003/0208200 | A1* | 11/2003 | Palanker | A61B 18/042 606/45 |
| 2007/0282407 | A1* | 12/2007 | Demarais | A61B 18/1492 607/113 |
| 2010/0130972 | A1* | 5/2010 | Yambor | A61B 18/14 606/34 |
| 2011/0306006 | A1* | 12/2011 | Holbeche | A61B 18/042 433/32 |
| 2012/0215216 | A1* | 8/2012 | Friedrichs | A61B 18/1206 606/38 |
| 2014/0074090 | A1* | 3/2014 | Lam | A61B 18/042 606/49 |
| 2014/0128936 | A1* | 5/2014 | Laufer | A61B 18/12 607/42 |

OTHER PUBLICATIONS

International Search Report (dated Oct. 26, 2016) for corresponding International App. PCT/CZ2016/050014.

* cited by examiner

PORTABLE DEVICE USED ESPECIALLY FOR ELECTROFULGURATION AND ELECTRODESICCATION

BACKGROUND AND SUMMARY

This portable device is used mainly for electrofulguration and electrodesiccation-especially for the removal of the skin deformities ranging from tiny growths on skin and on mucous membrane tumours as well as external forms of carcinoma and precarcenoma, warts and condyloma, scars and skin wrinkles. It is also used to stop bleeding, for the removal of blood-vessel based malformations on skin and mucous membranes and for smoothing of the skin especially in the facial area and the areas of neckline, neck, arms and stomach.

Electrocautheries running on alternating current are known from the practice. Known solutions are rather challenging when it comes to their production as well as maintenance and the initial costs are high.

Gas is composed of neutral atoms or molecules while the standard temperature is maintained. There are no particles which would lead electric current and that is why the gas is considered to be a good insulator. Inside the gas, collisions of atoms, ions and electrons occur. We consider these collisions inflexible because the energy levels inside the gas change. Inflexible collisions inside the gas cause ionisation, excitation, deexcitation and recombination of the ions and atoms and are caused by impact of free electrons and, although rarely, by ions. Aforementioned collisions can be described by Towsend's *Theory of Avalanche* in which the self-sustaining ionization mechanism of electrical discharges is explained.

If there is a DC voltage U between two metal plate electrodes, the electrical field will have an effect on the free electrons, which are naturally occurring in the air. Homogenous electrical field accelerate these electrons onto the positive plate (anode) and subsequently a collision with neutral atoms and molecules occurs. These accelerated electrons omits part of their kinetic energy to electrons of neutral atoms. During the ionization process by sufficiently big amount of energy of a neutral particle, a secession of a free electron occurs and a pair of electrons is created (hole). Hole is a place where there is insufficiency of electrons and that is why a positive charge is predominant. The amount of electrons exponentially increases with the path of the electron.

The electrons will flow towards the positive plate and the positive ions to the negative plate (cathode) where they create electrons. With the help of inflexible collision, they form electrons from the surface of the cathode. If the amount of the free electrons in the space between the cathode and the anode increases, the discharge itself will be created. The amount of the electrons should constantly increase but since the recombination of the electron pairs occurs (hole), the electric field between the electrodes decreases and subsequently stabilizes.

Aforementioned ionization of the gas was possible only due the input of the energy with the help of the electrical field, ultraviolet radiation, X-ray or cosmic radiation. This means that for the leading of the electrical conductivity of the gas a sufficiently big electrical field is necessary in order for this discharge to be called non-independent. In the electrical fields strong enough, the amount of the ions and electrons suitable for independent sustainability of the electrical field is created and such discharges are called independent.

Types of discharges that can occur during the increase or decrease of atmospheric pressure:

Arc Discharge—the characteristic feature is a high current density and lower voltage (approx. tens of volts) and also thermal emissions of electrons from a red-hot cathode. A thermal ionization of the surrounding air happens when the electrodes get separated by few millimeters.

Corona Discharge is created by a strong and non-homogenous electrical field. The overall current is insignificant. Incendiary voltage is dependent on the level of sharpness of the electrode. Most commonly, it occurs during the direct current and can burns on the border of spark discharge.

Spark discharge carry big currents through a smaller cross section ($\sim mm^2$) but last very shortly (around 10-7-10-3 seconds). A spark discharge is formed by very fast, dynamic and non-stationary energetic transforms and it is also accompanied by light flashes and acoustic expression. Predominantly, it is realized during the atmospheric pressure but a high density of electric field (around $E \sim 106$ V/nm) is also necessary.

Glow Discharge—electrons and ions are accelerated by means of electrostatic force between the electrodes happens during this type of discharge. It is necessary to have a sufficient intensity of the electric field (around $E \sim 3.106$ V/m0). Moreover, if we place the electrodes to a confined space of discharge tube, where the pressure is reduced, we are able to observe the glow discharge. In comparison to the arc discharge, glow discharge contains a low current and low temperature of electrodes as well as in the tube.

In the picture n. 3, it is possible to observe different types of electric discharges. In the first part of the curve (a) it is possible to see non-independent discharge during low input of the current. Once the line of incendiary voltage Uz is crossed, the electric field is big enough for acceleration of electrons and it is also big enough for sustaining an independent discharge—as possible to see in the second part of the curve (b). This is called the dark Towsend's Discharge. Each discharge is also accompanied by so-called corona, which is portrayed by part of the curve c. The fact is that a corona is present on the surface of each spark discharge.

Further part of the curve d portrays a glow discharge and part e of the curve represents the anomalous glow discharge, which occurs during higher current densities and temperatures.

Furthermore, an ignition of a spark discharge happens during an occurrence of high intensity of the electric field (around $E \sim 106$ V/m). If the current course is high enough, such discharge is called arc discharge (g). A spark channel entails a high conductivity and very small cross section (around 1 $mm^2$).

Later on, we will be dealing with plasma which occurs during any discharge present in the (ionized) gas. Lagmuir contributed to the discovery and diagnostics of the plasma in 1923. Lagmuir explored this form because he wanted to develop a tube that would be able to lead current during a low pressure—that is why it needed to be filled by a ionized gas. Plasma can be defined as ionized gas composed of electrons, neutral particles and molecules. It is created by the separation of the electrons from the electron shell of the atoms of gas or by the separation of the molecules (ionization). The temperature of the electrons in the plasma is much higher than the temperature of the ions and the neutral particles. That is why this type of plasma is named non-isothermic and must be artificially kept. In comparison to this, if the temperature of all the particles in the plasma is the same then the plasma will be isothermic.

If there is a circuit with two conductive plates and the voltage is constantly increased then, in the first phase, the circuit will follow the Ohm Law meaning that the current will be proportional to the voltage. In the next phase the saturation of the current occurs, which means that the current is constant. During further increase of the voltage, withholding cascade ionization occurs and the voltage exponentially increases. Last phase is caused by exceeding the level of threshold voltage UD, where the impact of the secondary electrons from the cathode will show. Since plasma contains free electric currents, it is also electroconductive.

Paschenkov Law means that the breakdown voltage Upr is dependent solely on the sum of pressure and the distance between cathode and anode. Pashenkov Law: Upr=f(p.d). Each of the functions of the specific gas has its minimum and was proven by experiments in 1889. If an alternating current is used instead of direct current then the formula is changed to:

$$Upr=f(p\times d, f\times d)$$

In the altered formula for alternating current, it is possible to see the frequency dependence. I is then possible to note that the breakdown voltage during the alternating current is lower than during the direct current.

In as far past as 3000 years BC in the Ancient Egypt, the utility of thermal cauters for the treatment of boils was described. Hippocrates described the method of destroying a neck tumour with the help of temperature. Later on, a hot iron was used for coagulation. The first usage of the thermal impact of direct current (DC) was described in the mid-17th century by Benjamin Franklin and John Wesley. They described indirect impact when a device was heated up by DC and subsequently attached to skin for a brief period of time.

At the beginning of the 19th century, a French physicist Becquerel used the DC led through a conductor, which very efficiently cauterized soft tissue at the point of contact.

In the second half of the 19th century, experiments with biological impacts of alternating current (AC) on tissue began. French physiologist Arsené D'Arsonval first started to apply spark discharge to a tissue. The aim was to destroy it by using thermoenergy. He named this process fulguration (lat. Fulgur means flash). The fact is that a presence of plasma (ionized gas) is necessary for fulguration.

For tens of years, alternating electrocauters with the usage of discharges have been used for similar indications.

Only alternating electrocauters will create a Shower of Sparks, which is a flow of sparks falling on an area of approx. 1 cm². Alternating electrocauters are used also for surgeries but have a much larger input of around 20 W, although it is also possible to set them to 0.1 W. Spark discharges generated here, on which sides coronas are created, radiate onto an area that is being treated. This area is usually at least 1 cm² wide. This is due to spark discharges generated by AC create a conical spark shower with a relatively large range.

Physiological body temperature is 36 to 37° C. During the illness, a body temperature can increase up to 40° C. without a structural damage to the cells or tissues. In the table below, an intercellular temperatures and the respective reaction of the organism is noted (see table 1).

TABLE 1

| The Reaction of the Body to the Change of the Temperature | |
|---|---|
| 50-60° C. | Cell death in approx. 1 to 6 minutes |
| 60° C. | Immediate cell death |
| 60-65° C. | Coagulation occurs |
| 65-90° C. | Denaturation of proteins |
| 90-100° C. | Desiccation happens |
| Over 100° C. | Leads to Vaporization |

A destruction of hydrothermal bonds between molecules of proteins occurs in between 60 and 65° C. and a homogenous coagulant occurs. That is why this process is called coagulation.

In the article *Fundamentals of Electrosurgery*, M. G. Murdo describes that in the period during which the temperature is lower than 60° C. thermo-based bonds are renewable if the temperature decreases locally. Dehydration and desiccation are processes during which the cells lose water through a membrane broken by a high temperature. It was proven that protein-based bonds become homogenous and they have gelatine structure.

Such impact on the tissue creates a possibility of closing of the tubular structures, such as blood-vessel, with the aim to stop the bleeding.

In such case, when the intracellular temperature increases over the 100° C., the water starts to vaporize in the intracellular environment. Subsequently due to high temperature, expansion and explosion of the cell occurs and the cellular content leaks to the extracellular environment. When the temperature rises over 200° C., the organic molecules are carbonized and so-called red coagulation occurs.

If DC or AC runs through the cells, which have a certain electrical resistance, a heating of cells due to the flow of the electric current occurs. A transformation from the electric energy to the heat occurs—a process which was first described by the physicist James Prescot Joule. The heat generated is dependent on the electrical resistance—the higher the heat the bigger the electrical resistance of the tissue.

For example, the resistance of a palmar skin is 100 kΩ, of the fat is 2 kΩ and muscle tissue is of 0.8 kΩ.

It is possible to achieve a sequence of spark discharges, which have a thermal effect on the skin, thanks to the usage of DC and AC. These sparks carry the thermal energy which increase the intracellular temperature of the cells. This process is called fulguration. Different intracellular temperatures can be achieved by setting up different intensity of the sequence of the spark discharges. By using this process, one is able to achieve different thermal effects to the cell leading up to carbonization.

Coagulation—the blood and tissues heat up during the flow of the electricity through them and that is why a denaturation of proteins and subsequent end to the bleeding occurs.

Desiccation is a process during which an intracellular liquid (water) heats up within the cells and vaporization of the water and the desiccation of the cell occurs.

Fulguration is then the process during which the destruction of the tissue occurs without any cuts necessary. This tissue superficially coagulates with gradually repetitive high-voltage sparks. However, these sparks have low current strength. If fulguration occurs, then the active electric wave is only present in 10% of the overall time of the activation. In majority of the cases, the process of fulguration is carried out by using the high-voltage AC, which is modulated with low operational cycle of 6%.

Vaporization means that the evaporation of the water from the cells occurs as a result of the electrical current being present.

In the recent past, fulguration with the help of high-voltage DC was used. In 1982, the first catheter ablation of AV node was used while using the current of the DC to lead the supraventricular tachycardia. A quadrupolar catheter was introduced straight to the heart through the inferior vena cava and the tissue was burnt while using the energy raging from 300 to 500 J. Then in 1984, the first ablation of posteroseptal pathway was done while using the current of DC. Following on the procedure of the American doctors, these ablation of AV node were done also in the Czech Republic while using the DC in the years 1983 till 1992.

Next in the line, Japanese doctors were doing the ablation of the AV node with the help of the DP to treat supraventicular tachycardias and also to treat the patients suffering from Wolf-Parkinson-White Syndrome to ablate posteroseptal accessory pathways. The article also mentions the usage of fulguration of the energy around 100 J to treat myocardial lesion.

Guy Fontaine in his article about his clinical experience with fulguration states that they have used the voltage of approx. 4 KV while using DC during the fulguration procedures. This was used to treat ventricular tachycardia. Later on in another article called *Catheter Design for Successful Fulguration Procedure*, Fontaine deals with the most suitable levels of the current and voltage used during the fulguration procedures. He notes the period of the effect being in the range of 4 till 6 ms with the voltage of the current being 2 to 3 kV and the DC between 40 to 50 mA. This means that while their carry outs, these fulgurations were ranging between 0.08n to 0.9 W during the treatment of the ventricular tachycardia. Due to technical difficulties later on, they had to modify there parameters to 60 to 80 mA of DC and performatively, they reached approximately 1.44 W.

Another team of doctors mentions using the low-energy cauters (0.1 mV, discharge of 20 to 36 W with the usage of the direct current for 15 to 30 seconds during the ablation AV node of the left ventricle).

The flow of the sparks effecting the skin causes the increase of intracellular temperatures—this phenomenon is described in the previous chapters and it is called fulguration. The carrier of the heat is the electric arc—the flow of the spark discharges, on which brinks a corona is created. The heat generated by the sequence of the discharges is proportionate to the input power of the electric current where the high voltage causes puncturation of the air and its ionization with a subsequent creation of the electric discharge.

The heat generated is proportional to input power and the time. In this case, it does not matter whether the sequence of the spark discharges is created by DC or if it is sinusoidal AC. In the case of any other but sinusoidal process, the alternativity would have to be taken into consideration. This is why it is possible to compare, for the uses of clinical evaluation, the electrocauters or other electrosurgical equipment working in the regime of fulguration with the help of applied input power and it does not matter whether it is a DC or AC excitation with sinusoidal progress. The original scientific descriptions are based on the directly excited electric discharges.

Paschenkov Law denominates the dependency of breakdown voltage of the gas as: Upr=f(p,d). This means that the breakdown voltage of the gas necessary for the creation of the independent discharge is dependent only on the sum of the pressure and the distance between cathode and anode.

Individual types of the gas differ in their functional dependency of the breakdown voltage on the gas pressure.

All the curves Upr/p×d have their minimum. Paschenkov Law was experimentally proven in 1889. If a different current than DC is used for the excitation, then Paschenkov Law modifies into Upr=f(p×d, f×d), where the f is frequency of the AC source.

Discharges of the DC were used for the first time in 1982 during the catheter ablation of the A V node (palliative performance). Later on in 1984, a catheter ablation using the discharge of DC was done. Applied method of catheter ablation of AV' node while using the discharge of the DC was used on the group of 5 patients with repeated attacks of supraventricular tachycardia in 1982. The ablation (destruction of the cells) was achieved with the help of electric discharges. This method showed that it is possible to vaporize the cells with relatively wide range of aim and without any damage o to the surrounding tissue using the DC. This was due to the fact that the spark channel of the arc discharge generated by the DC has a cross section of 1 mm$^2$.

The thermal effects of the direct current and sinusoidal AC, which excitates spark discharge, are the same. The electric work, which is done by the DC between the two places in the electrical circuit at a given time is equal to the work necessary for the transmission of the electric discharge Q during the given time t. During the constant current passing throughout the circuit it is given that: We=Q·t=U·I·t Electricity passing through the circuit is invoked by the movement of the electric discharges doing the work. In metals, the carriers of this discharge are free electrons.

Due to their interaction, meaning the collision of the electrons with the atom grid, the conversion of the kinetic energy to heat occurs, which will then increase the temperature of the material. This heat, wildly addressed as Joule's Heat, is equal to the energy of the electric current passing through the conductor.

The relation between the Joule's Heat Qj, the current I and the resistance of the conductor R is called Joul-Lenz Law:

$$Qj=U·I·t=R·I2·t=(U2/R)·t=P·t$$

It then true for the power dissipation on the conductor or the resistor that: u: P=U·I=U2/R=R·I2

When it comes to the AC, the calculation is more complex since the magnitude of the voltage and the current is constantly changing with time and there are also two phase shifts between the two. That is why the multiplication by the cos {Θ}, which is so-called power factor, is added to the calculation.

The manufacturers state already averaged values of voltage and current and related performance on their devices. This means that the work of the excitative spark discharge is equal to the heat, which is generated by the flow of sparks and that is approximately equal to the performance during a certain period of time, as already described. That is why the thermal impact of the AC and DC could be considered equal.

According to an aspect of the invention, a portable device used especially for electrofulguration, electrodesiccation and electrocoagulation is provided. This device includes a source of energy and applicator. The nature of this device is that it entails the source of DC with the maximal current of 1 mA and the voltage of 0.8 to 12 kV, and the applicator is provided with very exact aiming finish. The patient is conductively connected with the equipment via disposable grounding electrode while the voltage of the discharge between the working electrode and the surface of the skin is between 0.3 to 4.0 W.

The applicator is also provided with gilded removable tip and eventually also with long-distance glass tube. The inner diameter of the glass tube is, with an advantage, 0.3 millimetres.

Battery is the source of the direct current.

Technological solution is the device that is power supplied by DC for medical purposes-mainly for small dermatological and surgical procedures. Its effects are achieved due to continuous spark discharges in combination with thermoenergy, which is able to destroy skin cells when the intensity is set for high values. Continuous spark discharge is very narrow—it operates over the area treated in spots and that is why the healthy tissue surrounding the area is not damaged, which is in contrast with the high-frequency electrosurgical units and electrocauters power supplied by AC. Spark discharge generated by them widens conically in the direction of the surface of the tissue treated.

Spark discharge itself occurs due to high voltage in the values varying between 4 to 12 kV. The output p of the discharge between the working electrode—the tip of the equipment and the surface of the skin—is in the range between 0.4 and 4.0 W.

Electrical circuit is closed by grounding strap on the arm of the patient. It is used for electrofulguration and electrodesiccation during which the destruction of the cells is the aim of the procedure. The usage of such high intensity of the spark discharge must be confirmed by the user after the initial setting.

The setting of the parameters of the device before and after the procedure is done by touch display. In the range of power of 0-1.0 W, they are not able to defect the cell permanently but when the values of the power increases (between 1.0 to 4.0 W) a coagulation, desiccation, fulguration and vaporization occurs. The intensity of these power outputs increases to the levels of 6, 7 and 8. The performance of individual levels is derived from the performance characteristics—please see tab. 2.

TABLE 2

The Relation between Power and Level

| Level | Power (W) |
|---|---|
| 6 | 1.2 |
| 7 | 1.6 |
| 8 | 1.8 |

Intended Purpose of the Use—Indication: Indication for the Treatment by the Device Jett Plasma Lift Medical.

In the case of basal cell carcinoma and carcinomas, the treatment is only possible if there was a histological examination.

angioma senilis
verruca seborrhoica
verruca plane
angiokeratoma
teleangiektasie
lentigo
fibroma molle
keratocanthoma
conydolamata accuminatum
moluscum contagiosum
verrucae vulgaris
verrucae filitormes
pulpitis
naveus capillaris
naveus araneus
basalioma superficiale
carcinoma spinocellularis
lymphangioma
keratosis actinica
keratosis senilis
kerstosis sebborhoica Moreover, it is the reduction of the wrinkles and skin.

Next possibility is its use in gynecology, proctology, urology, stomatology and in other fields in which hemostasis is necessary as well as removal of small deformities and tumors and electrodesiccation of tissues.

Spark (plasma) discharge is very narrow, it operates over the area treated in spots and that is why the healthy tissue surrounding the spot treated is not damaged, which is in contrast with the high voltage electrosurgical units. The spark discharge of these units widens conically in the direction of the surface of the tissue treated.

The inspection of patient being grounded—the system checks if the patient is connected with the device by self-adhesive electrodes. If the grounding electrode is disconnected from the patient, the system automatically turns off and there will be the word TAPE shown on the screen. In the past, burns used to occur during the usage of AC electrocautheries, if the patient was disconnected.

A portable electrocauter with touch screen—a dual processor system—offers the user a full comfort and it is possible to move the device from place to place thanks to it light weight at the same time. Easy-to-use touch screen alongside with the system of automatic control is very user-friendly.

The cover of the device is made of high quality plastics, which was processed by CNC technology, that increases the utility value and the overall safety of the device.

The device, based on this technical solution, uses thermo- and electro-effects of the spark discharges that are excitated by DC without the tip of the device touching skin. This effect of the DC is generally called electrofulguration. When the contact between the tip of the equipment and the skin occurs, thermal effects of the discharge on the skin happen directly in the cells. At the point of contact, the increase of the temperature within the cell occurs and the water is transformed into vapour. This effect of the DC is generally called electrodesiccation.

BRIEF DESCRIPTION OF THE DRAWINGS

The portable device, constructed especially for the electrofulguration and electrodesiccation based on this invention, will be described in more detail at the example of actual realization with the help of the drawings attached in which.

DETAILED DESCRIPTION

Figure 1:
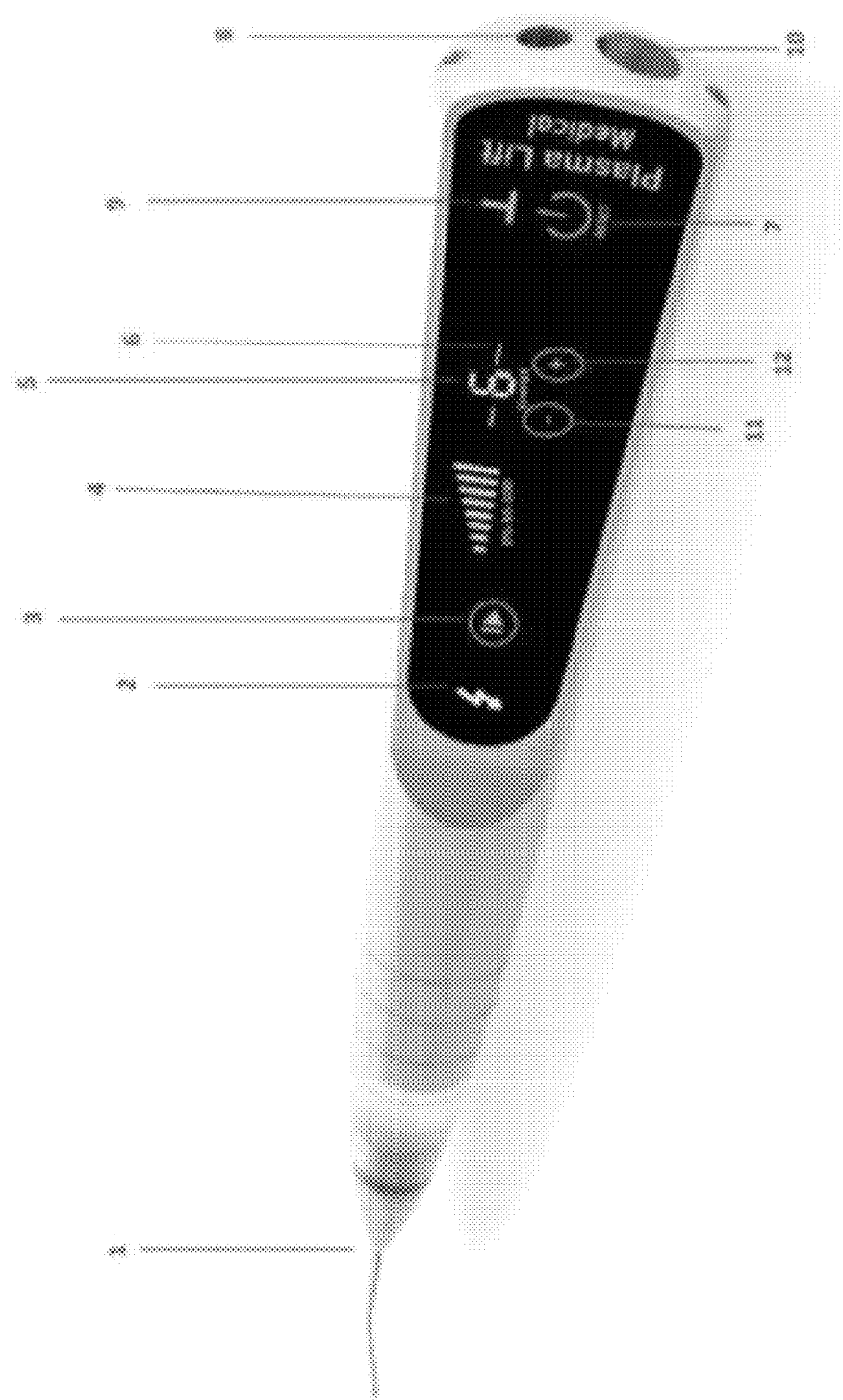
FIG. 1 shows a device in axonometric perspective.
Figure 2:
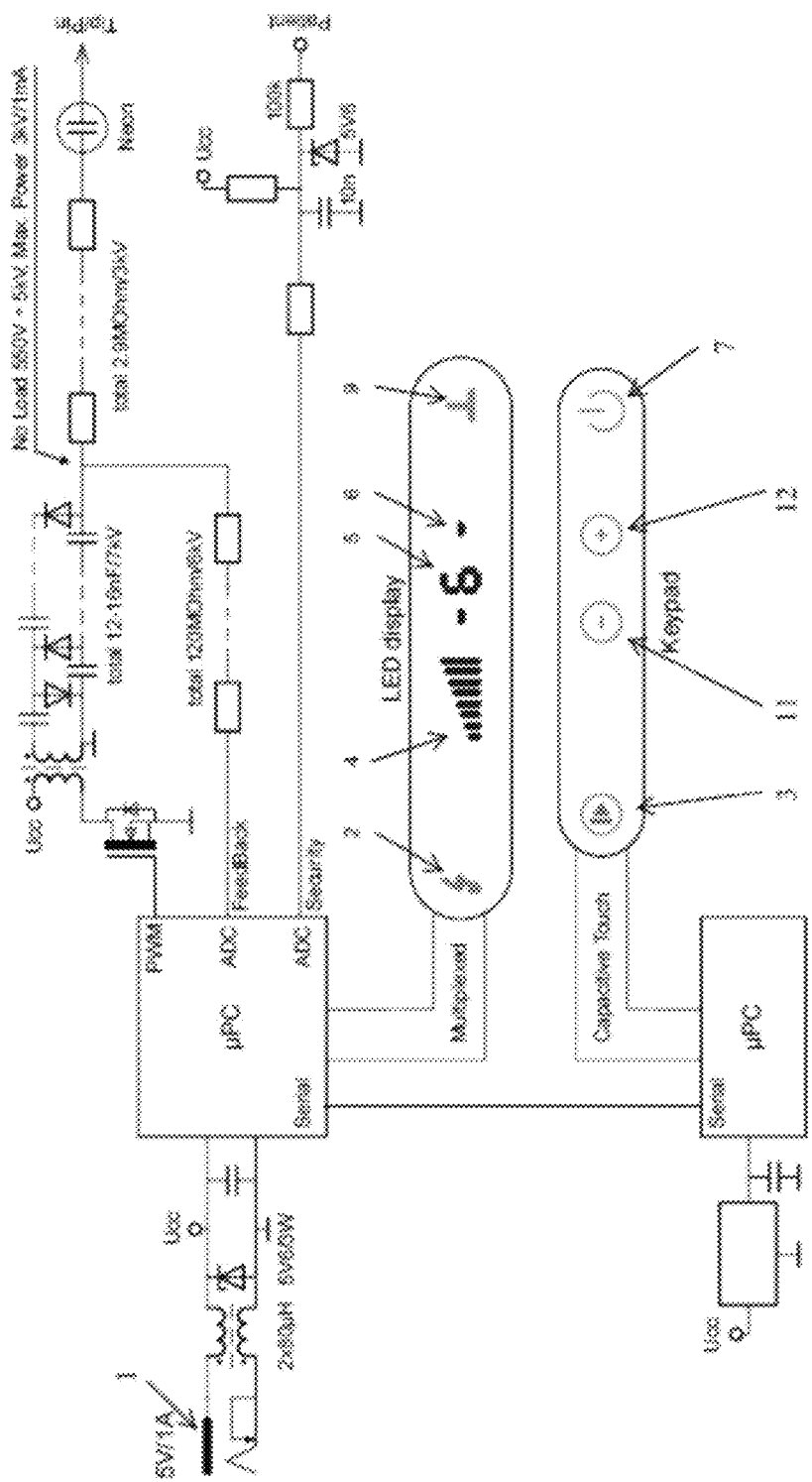
FIG. 2 is a block diagram of the device.
Figure 3:
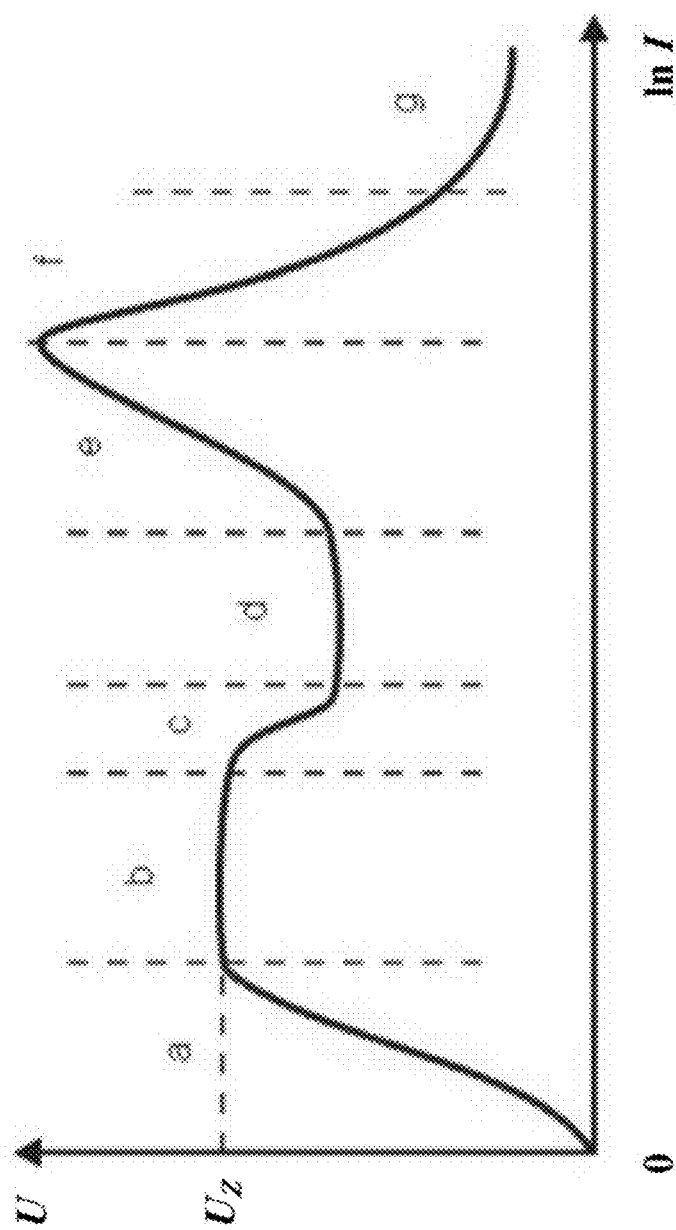
FIG. 3 shows different types of electrical discharges.

Portable device, used specifically for electrofulguration and electrodesiccation is composed of applicator 1 with a precisely aiming end, which has a gilded and detachable tip. There is an indicator 2 of the spark discharge (FLASH), button 3 for Play/Pause, which ignite and extinguish the spark discharge. Moreover, there is the indicator 4 of the effectivity of the spark discharge (this is the electricity that passes through the patient), then indicator of the intensity of the spark discharge 5 (it is marked Energy on the display) and a dash 6 before and after the numeric value of the intensity of the spark discharge. It also entails On and Off Buttons 7, socket 8 for connecting the grounding cable to the neutral electrode that is conductively connected with the patient and an On indicator 9. The equipment also entails a socket 10 used for plugging into adapter, a button 1 for switching into lower intensity of the discharge and a button 12 for setting a higher intensity of the discharge.

Portable electrocauter is provided with the source of DC with the maximal current of 1 mA and voltage 0.8 to 12 kV, the applicator 1 is provided with exact aiming finish and the patient is conductively connected with the device though disposable grounding electrode, while the output power between the working electrode and the surface of the skin is in the range of 0.3 to 4.0 W.

The applicator 1 is provided with gilded removable tip. The source of the DC is battery.

Spark discharge of the tip is linked, which is in contrast to electrocauters on AC.

Standard Technical Parametres:
Electrical Supply: 100 to 240 VAC/50-60 Hz
Class of Protection against Electric Shock: II
The Type of Device: with applied part type BF
The Type of the Supply Source: DA 12-050EU-M, manufacturer EMERSON
Power Supply Input: 100-240 V/50-60 Hz
Power Supply Output: 5 VDC, max. 2.0 A
Output of Power Supply: max. 12 W
The Voltage of the Generator of the Plasma Discharge: 0.8-12 kV
Output of Plasma Discharge: 0.3-4.0 W
Detection of the Functionality between the Neutral Electrode and the Patient: system SCS
Automatic Turning Off of the High Voltage of the Tip of the applicator: after 20 seconds
Accelerated Lowering of the Voltage to 0 on the Tip of the applicator after Turning Off: after 1 sec
Dimensions: length 245, width 45 mm
Weight: approx. 350 g
The Level of Coverage: IP2X A portable device used especially for electrofulguration and electrodesiccation is equipped with applicator 1 which is provided with long-distance glass tube, in accordance with CZ utility model n. 27650. Using the long-distance glass tube achieves that the constant distance of 2 mm from skin of the patient is sustained. This means that, as a first device on the world, it is able to produce the spark shower in a very thin volume and at the same time keep the distance of 2 mm from the skin.

A great advantage is the inner diameter of the glass tube, which is 0.3 mm. At such a value of the inner diameter of the glass tube, the spark discharge can be precisely aimed. Spark discharge burns when the intensity is at the levels 7-8 while the distance is 4 mm, which means that the head of the tube will be 2 mm over the area treated. Spark discharge is even more precisely aimed due to the glass tube. The idea of aiming the spark tube by glass tube is to be protected.

System automatically evaluates if the patient (client) is connected to the equipment via self-adhesive electrode. This way, possible burns can be avoided, which could occur if the patient is disconnected from the device. The method of the identification is to be protected—as per the block schema.

Electrocauter, based on this invention, will find its use in various fields of the medicine, especially for treatment of pathologically changed tissues. It could be used in dermatology but also in stomatology, surgery, gynecology, proctology, urology, otorhinolaryngology and many other fields where it is necessary to get rid of pathological tissues or to destroy cells by means of electrodesiccation or where there is necessary to stop a small bleeding. It is meant to be used for the treatment of face for precise removal of skin artefacts or to perform fulguration-type of microburns to the skin around the wrinkles. The skin will smooth during the healing of these microburns.

The invention claimed is:
1. A portable medical device, comprising:
a source of energy, and
an applicator, wherein:
the source of energy is a direct current (DC) energy with a maximal current of 1 milliamp (mA) and voltage of 0.8 to 12 kilovolts (kV), and
the portable medical device comprises a disposable grounding electrode adapted to conductively connect a patient to the portable medical device such that an output of a continuous spark discharge between a working electrode and a surface of the patient over an entire period of time for performing an electrocautery operation is a DC output in the range of 0.3 to 4.0 Watts (W), wherein further:
the applicator is provided with a gilded removable tip and with a long-distance glass tube having an inner diameter of 0.3 millimeters (mm).
2. The portable medical device according to claim 1, wherein the source of the DC energy is a battery.
3. The medical device of claim 1, further including an indicator of effectivity of spark discharge and an indicator of intensity of the spark discharge, both corresponding to the output of the continuous spark discharge.

* * * * *